(12) United States Patent
Ito et al.

(10) Patent No.: US 7,339,022 B2
(45) Date of Patent: Mar. 4, 2008

(54) PEPTIDE FRAGMENT OF LYVE-1 AND ANTIBODY AGAINST THE SAME

(75) Inventors: Kinji Ito, Tokyo (JP); Toshiharu Ishii, Tokyo (JP); Yuri Fukasawa, Tokyo (JP)

(73) Assignee: Oriental Yeast Co., Ltd., Tokyo (JP)

( * ) Notice: Subject to any disclaimer, the term of this patent is extended or adjusted under 35 U.S.C. 154(b) by 0 days.

(21) Appl. No.: 10/548,495

(22) PCT Filed: Mar. 11, 2004

(86) PCT No.: PCT/JP2004/003231

§ 371 (c)(1),
(2), (4) Date: Sep. 9, 2005

(87) PCT Pub. No.: WO2004/081035

PCT Pub. Date: Sep. 23, 2004

(65) Prior Publication Data

US 2006/0127396 A1    Jun. 15, 2006

(30) Foreign Application Priority Data

Mar. 14, 2003    (JP) ............................. 2003-070568

(51) Int. Cl.
*A61K 38/00* (2006.01)
(52) U.S. Cl. ....................... 530/300; 530/300
(58) Field of Classification Search ..................... None
See application file for complete search history.

(56) References Cited

U.S. PATENT DOCUMENTS 5,942,417 A * 8/1999 Ni et al. ..................... 435/69.1
6,368,794 B1 * 4/2002 Daniel et al. .................. 435/6
2002/0119130 A1   8/2002 Eaton et al.

FOREIGN PATENT DOCUMENTS

WO    WO-03/006104    1/2003

OTHER PUBLICATIONS

Puri et al., J Immunol, vol. 139, 2996-3002, 1987.*
Laakkonen et al., Nature Medicine, vol. 8, p. 751-755, 2002.*
Prevo et al., JBC, vol. 276, p. 19420-19430.*
Abbas et al., cellular and molecular immunology, 4th edition, 2000.*
Prevo et al., JBC, vol. 276, p. 19420-19430, 2001.*
International Search Report dated May 18, 2004, 6 pages.
Jackson, D.G., "The Lymphatics Revisited: New Perspectives from the Hyaluronan Receptor LYVE-1," Trends Cardiovasc Med., Jan. 2003; 13(1):1-7 (7 pages).
Straume, O., et al., "Independent Prognostic Impact of Lymphatic Vessel Density and Presence of Low-Grade Lymphangiogenesis in Cutaneous Melanoma," Clin. Cancer Res., Jan. 2003; 9(1):250-6 (7 pages).
Cursiefen, C., et al., "Lymphatic Vessels in Vascularized Human Corneas: Immunohistochemical Investigation Using LYVE-1 and Podoplanin," Investigative Ophthalmology & Visual Science, 2003, vol. 43, No. 7, pp. 2127-2135 (9 pages).
Akishima, Y., et al., "Immunohistochemical Detection of Human Small Lymphatic Vessels Undeer Normal and Pathological Conditions Using the LYVE-1 Antibody," Virchows Arch., Feb. 2004, 444(2):153-7 (5 pages).
Supplementary European Search Report for Application No. EP04719660 dated May 24, 2006 (2 pages).
Banerji Suneale et al.: "Lyve-1, a new homologue of the CD44 glycoprotien, is a Lymph-specific receptor for hyaluronan," The Journal of Cell Biology, Rockefeller University Press, US, vol. 144, No. 4, Feb. 22, 1999, pp. 789-801 (13 pages).
DATABASE Geneseq (online), Dec. 10, 2002, "Human secreted/tansmembrane protein PRO263", retrieved from EBI accession No. GSN: ABG95853, Database accession No. ABG95853 (9 pages).
Podgrabinska, Simona et al: "Molecular characterization of lymphatic endotherlial cells," Dec. 10, 2002) Proceedings of the National Academy of Sciences of the United States of America, vol. 99, NR. 25, pp. 16069-16074 (6 pages).

* cited by examiner

*Primary Examiner*—Shanon Foley
*Assistant Examiner*—Lei Yao
(74) *Attorney, Agent, or Firm*—Osha Liang LLP (57) ABSTRACT

It is intended to provide a specific peptide fragment of LYVE-1 which can serve as an epitope of a lymphatic vessel-specific antibody, and an antibody recognizing the above peptide fragment. A peptide fragment comprising an amino acid sequence:
Ser Lys Lys Thr Asp Lys Asn Pro Glu Glu Ser Lys, or the peptide fragment in which an amino acid as a linker to the C-terminal or the N-terminal thereof is added.

2 Claims, 4 Drawing Sheets

SEQUENCE LISTING

```
<160> NUMBER OF SEQ ID NOS: 2

<210> SEQ ID NO 1
<211> LENGTH: 12
<212> TYPE: PRT
<213> ORGANISM: Homo sapiens

<400> SEQUENCE: 1

Ser Lys Lys Thr Asp Lys Asn Pro Glu Glu Ser Lys
1               5                   10

<210> SEQ ID NO 2
<211> LENGTH: 36
<212> TYPE: DNA
<213> ORGANISM: Homo sapiens

<400> SEQUENCE: 2
tcaaagaaaa ctgataaaaa cccagaagag tccaag                              36
```

PEPTIDE FRAGMENT OF LYVE-1 AND ANTIBODY AGAINST THE SAME

TECHNICAL FIELD

The present invention relates to a specific peptide fragment of LYVE-1 (Lymphatic Vessel Endothelial hyaluronan receptor-1), a receptor for glycosaminoglycan hyaluronan which is an extracellular matrix and frequently appears during healing of wound in inflammation, to an antibody against said peptide fragment, and to the use thereof. Especially, the peptide fragment and the antibody thereto of the present invention are useful for the histological certification of lymphatic vessels and the immunohistochemical inspection for malignant invasion into the lymphatic vessels.

BACKGROUND ART

Hyaluronic acid, one of the extracellular matrices, is an important factor related to chemotaxis, wound healing, tumor metastasis and the like, and exists in almost all cells of the living tissues. The intercellular communication mediated by the hyaluronic acid and hyaluronic acid binding receptors on the cell surface is one of the important means of the intercellular interaction. Recently, the hyaluronic acid also has been reported to have ability as an activating factor of NF (nuclear factor)-κB, one of the intranuclear transcription factor, and as an angiogenesis promoting factor, as well as a chemotaxis factor.

Several hyaluronic acid binding receptors located on cell membrane for example, CD44 (one of Clusters of Differentiation, i.e., lymphocyte antigen groups), LYVE-1 (lymphatic vessel endothelial HA receptor), RHAMM (Receptor for Hyaluronan-Mediated Motility), and LEC (Liver Endothelial Cell clearance) receptor have been hitherto identified. Among these hyaluronic acid binding receptors, LYVE-1 has been found to be a receptor comprising 322 amino acid residues (see, J. Cell Biol. 144, 789-801 (1999)).

It has been clarified that mRNA of LYVE-1 is expressed in almost whole body, such as the spleen, the lymph node, the fetal liver, the heart, the lung and the like, and that the LYVE-1 receptors are localized on the endothelium of the lymphatic vessel in those tissues. Therefore, it is considered that the LYVE-1 may be used for identifying the lymphatic vessel which is difficult to be discriminated morphologically from the blood vessel.

For example, in the lymphogenous metastasis of malignant, the processes of metastasis are: after invasion to surrounding tissues, the tumor infiltrates the lymphatic vessel wall destructively and penetrates into the lymphatic vessels, where it is transferred lymphogenously, to the region distant from the primary focus. In these invading processes, the host tissues involving the lymphatic vessel are broken.

Accordingly, if detailed observations of the lymphatic vessels in the pathological tissues are obtained, then they may give us useful histopathology of the destructive and invasive growth of the tumor.

Until now, there have been several reports having observed the image of the tumor invading into lymphatic vessels by infiltrating through the lymphatic vessel wall destructively (see: Takazawa H., An electron-microscopic study on the transplanted part of lymphatic vessels in the experimental formation of lymphatic metastasis (in Japanese), General meeting news of Japan Cancer Association, 30, 296(1971); Araki K., An electron-microscopic study of the initial stage of the cancer invasion and the lymphatic vessel infiltration: an observation on an N-Methyl-N'-nitro-N-nitrosoguanidine (MNNG) induced rat stomach cancer (in Japanese), Okayama Med. J., 91, 659-669 (1979); James N., et al., Growth and metastasis of Lewis lung carcinoma in the footpad of mice, Expl. Cell Biol., 56, 221-228 (1992); Carr I., et al., The fine structure of neoplastic invasion: invasion of liver, skeletal muscle and lymphatic vessels by the Rd/3 tumour, J. Pathol., 118, 91-99 (1976); Paku S., et al., Ultrastructural analysis of experimentally induced invasion in the rat lung by tumour cells metastasizing lymphatically, Anticancer Res., 6, 957-966 (1986)).

These reports, however, are the studies at the cell level making use of electron microscopes. There have been no reports on tissue level having observed scenes of tumor invasion into the lymphatic vessels in a tissue.

On the other hand, various staining methods of tissues or the like for observing pathological images of pathological tissues by staining have been developed. For example, immunohistochemical staining techniques such as an enzyme antibody technique or the like are excellent in the specificity and reproducibility, and the method according to the present invention belongs to this category. However, no methods have hitherto been known that it selects the lymphatic vessels as a staining target and stains it selectively.

DISCLOSURE OF THE INVENTION

Problems to be Solved by the Invention

An object of the present invention is to provide a specific peptide fragment of LYVE-1 which can be an epitope for a lymphatic-vessel-specific antibody, and to provide an antibody recognizing the peptide fragment. Another object of the present invention is to provide a method to stain specifically the lymphatic vessels using the antibody obtained based on the specific peptide fragments of the LYVE-1, in other words, a method of obtaining pathological findings about the destructive and invasive growth of the malignant based on the stained image.

Means to Resolve the Problems

In order to resolve above mentioned problems, the inventors of the present invention selected various peptide fragments from among the amino acid sequence of LYVE-1, and connected to the selected peptide fragments, an auxiliary group for immunogen recognition (such as KLH: keyhole limpet hemocyanin, and the like) through an appropriate amino acid as a linker (such as cysteine) and an appropriate spacer (such as MBS (m-maleimidebenzoyl-N-hydroxysuccinimide ester) and the like); then, immunized rabbits using these as antigens. Antibodies were extracted from the immunized rabbit serum and were purified, and then immunostaining was conducted making use of a removed human tissue.

Then, when the above mentioned antibody preparation and the immunostaining were conducted, among various peptide fragments tested, a peptide fragment corresponds to 297th to 308th in the registered amino acid sequence at GenBank with the Accession number AF118108, represented by the following sequence:

(SEQ ID NO:1)
Ser-Lys-Lys-Thr-Asp-Lys-Asn-Pro-Glu-Glu-Ser-Lys, which is located within the region in the amino acid sequence of LYVE-1 and in the region satisfying the following four conditions: (1) hydrophilic, (2) not glycosylated, (3) having β-turn structure, and (4) intracellular, was found to give a staining specific to the lymphatic vessel. Moreover, based on the results of the immunostaining using the antibody according to the present invention, a detailed profile of the lymphatic vessels in the living tissue could be obtained. Also, in particular, pathological findings could be obtained about the early-stage destructive and invasive growth of the malignant, which had been usually difficult to confirm.

That is to say, the present invention relates to a peptide fragment comprising an amino acid sequence represented by SEQ ID NO:1, or to said peptide fragment with an amino acid added to the C-terminal or N-terminal thereof as a linker, and also relates to an antibody against said peptide fragments.

The present invention also relates to the DNA fragment encoding the peptide fragment represented by above SEQ ID NO:1, which is represented by the following sequence:

```
                                              (SEQ ID NO:2)
TCA AAG AAA ACT GAT AAA AAC CCA GAA GAG TCC AAG.
```

The present invention also relates to the above menthioned antibody specific to Lymphatic Vessel Endothelial hyaluronan receptor-1 (LYVE-1).

The present invention also relates to a peptide fragment consisting of an amino acid sequence in which deletion, replacement, or addition of one or several amino acids is made to the amino acid sequence of SEQ ID NO:1, and being recognized by the above mentioned antibody, or relates to said peptide fragment wherein an amino acid is added to the C- or N-terminal thereof as a linker; and also relates to a DNA fragment encoding the same.

Further, the present invention relates to the use of the above mentioned peptide fragment for preparing the above mentioned antibody.

In addition, the present invention relates to a human lymphatic vessels immunostaining composition and a human lymphatic vessels immunostaining reagent kit, characterized by containing the above mentioned antibody.

Here, said human lymphatic vessels immunostaining reagent kit may contain, other than the antibody of the present invention, a blocking reagent for an intrinsic peroxidase such as 3% hydrogen peroxide water or the like, a biotin-labeled antibody against the rabbit immunogloblin, a peroxidase-labeled streptavidin, substrate buffer solution such as Tris-HCl buffer solution or the like, color reagent such as DAB (3,3'-diaminobenzidine tetrahydrochloride) and the like, and/or substrate reagent such as 0.8% hydrogen peroxide water or the like.

Also, the present invention relates to a method for specifically immunostaining removed human lymphatic vessels, using the antibody of the present invention.

Moreover, the present invention also relates to a method for measuring the degree of malignant invasion by a specific immunostaining of the human lymphatic vessels using the antibody of the present invention, and a method for diagnosing the degree of malignancy of the malignant by measuring said degree of invasion.

Furthermore, the present invention also relates to an isolation and purification of the human lymphocytes using the antibody of the present invention, that is, a preparative isolation of the lymphatic vessel cells and precursor cells thereof. For the preparative isolation of cells, a cell sorter, the magnetic cell separation method, or the like can be used, for example. The isolated cells may be used for example, for lymphatic vessel neogenesis therapeutics, aimed to reduce the lymphatic vessel edema.

Preparation of the Peptide Fragment

The peptide fragment of the present invention can easily be prepared using a commercially available automatic peptide synthesis apparatus.

Preparation of the Antigen

In order to increase the antigenicity of the peptide fragment, a carrier protein is combined to the peptide fragment. For the combination of the peptide fragment and the carrier protein, a linker and a spacer are used in order to avoid inhibition of the antigen-antibody reaction due to steric hindrance or the like. That is, it is advantageous to use a conjugate, a peptide fragment-linker-spacer-carrier protein, as an antigen.

As for the linker usable for preparing the antigen, an amino acid having the ability to mediate the combination of the peptide fragment and the spacer, that is, with the linking ability, such as cysteine, glutamic acid, tyrosine and the like can be exemplified, and cysteine is preferable.

Here, the linker can be combined with either C-terminal or N-terminal of the peptide fragment, but preferablly, is combined with N-terminal.

The reasons why it is preferable that the linker is combined with the N-terminal is as follows. The peptide fragment is synthesized from the C-terminal. Thus, by combining the linker with the N-terminal, a peptide fragment with incomplete length can be prevented from being combined with the carrier protein. Also, if there is a cysteine at the C-terminal, racemization may occur, so that a prevention measure thereof may be necessary, and the yield may become lower.

As for the spacer usable for preparing the antigen, crosslinking reagents, such as MBS (m-maleimidebenzoyl-N-hydroxysuccinimide ester), SMCC (succinimidyl 4-(N-maleimidemethyl)cyclohexane-1-carboxylic acid), Sulfo-SMCC (sulfosuccinimidyl 4-(N-maleimidemethyl) cyclohexane-1-carboxylic acid), or Sulfo-MBS (m-maleimidebenzoyl-N-hydroxysulfosuccinimide ester) or the like, can be exemplified, and MBS is preferable.

Further, as for the carrier protein usable for preparing the antigen, proteins such as bovine albumin, ovalbumin, myoglobin, and keyhole limpet hemocyanin (KLH) and the like can be exemplified and preferablly, KLH is used advantageously.

Coupling of the peptide fragment with the linker can be easily conducted by means of an automatic peptide synthesizer. Also, coupling with the spacer and the carrier protein can be easily conducted by the conventional methods.

Preparation of the Antibody

The antigen obtained by the above mentioned antigen preparation is emulsified together with an adjuvant and used to immunize animals. After immunization, the animals are bled and the antiserum is isolated. From this antiserum, the antibody is fractionated by the affinity chromatography method.

For preparing an antibody, a mouse, a rabbit, a rat, a sheep and the like, can be used, for example, as the animals to immune, and preferable animal to immune is a rabbit or a sheep.

Also, the antibody can be prepared as monoclonal antibody by means of general monoclonal antibody preparing procedure.

Examination of Immunospecificity of the Antibody

Protein sample was obtained by a conventional method from cells expressing the LYVE-1 gene, transferred on nylon filter by Western blotting, and used as a filter sample. Plural filter samples were prepared. A part of the filter samples were reacted with the LYVE-1 antibody of the present invention, and the remaining filter samples were reacted with a test solution containing the LYVE-1 antibody of the present invention being reacted in advance with the peptide used for immunization. The filters subjected to the reaction were stained by the general staining method such as the one using an enzyme-bound second antibody.

As a result, a band corresponding to the coupled entity of LYVE-1 and the LYVE-1 antibody was confirmed on the filter sample reacted with the LYVE-1 antibody of the present invention, while such a band was not observed on the filter sample reacted with the test solution containing the LYVE-1 antibody of the invention having been reacted in advance with the peptide used in immunization, and thus the LYVE-1 antibody of the present invention was confirmed to be specific to LYVE-1.

Tissue Staining

A fixed paraffin section or a frozen section of normal human tissue was prepared and reacted with the LYVE-1 antibody of the present invention. It was then stained by the general staining method such as the enzyme antibody technique, fluorescent antibody technique or the like.

As a result, only the lymphatic vessels in the tissue sections were stained, and any other parts were not stained. This result indicated that the LYVE-1 antibody of the present invention is an antibody which recognizes specifically the lymphatic vessels. Moreover, the finding that, in the samples on which the tumor invasion was observed, the parts positive to the LYVE-1 antibody were the lymphatic vessels, also indicated that the LYVE-1 antibody of the present invention is specific to the lymphatic vessels.

The present invention is explained by the examples more concretely as follows.

BRIEF DESCRIPTION OF THE DRAWINGS

| Measured by PE Biosystems Voyager System 1162. | |
|---|---|
| Mode of operation: | Linear |
| Extraction mode: | Delayed |
| Polarity: | Positive |
| Acquisition control: | Manual |
| Accelerating voltage: | 20000 V |
| Grid voltage: | 94% |
| Guide wire 0: | 0.1% |
| Extraction delay time: | 225 nsec |
| Acquisition mass range: | 500 to 3000 Da |
| Number of laser shots: | 128/spectrum |
| Laser intensity: | 2119 |
| Calibration type: | External |
| Calibration matrix: | a-Cyano-4-hydroxycinnamic acid |
| Low mass gate: | 500 Da. |
| Digitizer start time: | 14.2498 |
| Bin size: | 2 nsec |
| Number of data points: | 50000 |
| Vertical scale: | 1000 mV |
| Vertical offset: | 1% |
| Input bandwidth: | 100 MHz |
| Sample well: | 34 |
| Plate ID: | 100 |
| Serial number: | 1162 |
| Instrument name: | Voyager-DE |
| Plate type filename: | C:\VOYAGER\100 well plate.plt |
| Lab. name: | PE Biosystems |
| Absolute x-position: | 18588.6 |
| Absolute y-position: | 30956 |
| Relative x-position: | 1761.12 |
| Relative y-position: | −1111.46 |
| Shots in spectrum: | 31 |
| Source pressure: | 3.296e-007 |
| Mirror pressure: | 0 |
| TC2 pressure: | 0.01811 |
| TIS gate width: | 30 |
| TIS flight length; | 940 |

FIG. 2a is an immunostained picture of a cos 7 cell in which the whole length LYVE-1 cDNA was incorporated and expressed, stained by the LYVE-1 antibody. In FIG. 2a, LYVE-1 is observed to be expressed mainly on the cell membrane on the cell surface, and also slightly expressed in the cytoplasm.

FIGS. 2b-2d are stained pictures of the serial sections of the stomach tissue. FIG. 2b is a stained picture by Hematoxylin-Eosin staining (HE staining), FIG. 2C is a stained picture by the LYVE-1 antibody, and FIG. 2d is an immunostained picture using the vWf antibody.

FIGS. 2e-2m are immunostained pictures of various human normal tissues using the LYVE-1 antibody. FIG. 2e is the resultant picture of the esophagus, FIG. 2f is of the colon, FIG. 2g is an extensive magnification of a LYVE-1 positive lumen in FIG. 2f, FIG. 2h is of the heart, FIG. 2i is of the lung, FIG. 2j is of the kidney, FIG. 2k is of the prostate gland, FIG. 2l is of the ovarium, and FIG. 2m is of the pancreas tissue.

FIGS. 2n-2q are stained pictures of main organs having antrum structures, among human normal tissues. In FIG. 2n, LYVE-1 expression is observed on the liver sinusoid endothelial cells, and FIG. 2o is an extensive magnification thereof. FIG. 2p shows observed LYVE-1 expressions on the endothelial cells of the spleen splenic sinus, and FIG. 2q shows those on the endothelial cells and on the reticular fibers of the lymphatic vessels in the lymph node.

FIGS. 2r-2x are stained pictures of lesioned tissues in the human malignant tumors. Among them, FIGS. 2r-2t are related to tissues of esophageal carcinoma. In FIG. 2r, tumor cell aggregations of esophageal carcinoma (squamous carcinoma) are observed in the LYVE-1 positive lumina, indicating the lymphatic vessel invasion, and FIG. 2s is an extensive magnification of said part. FIG. 2t is a stained picture by the vWf antibody, using a serial section of FIG. 2r.

FIGS. 2u and 2v regard the tissues of lung cancer. FIG. 2u, shows tumor cell aggregations of the lung cancer (adenocarcinoma) in the LYVE-1 positive lumina in the connective tissues in the circumference of the lung bronchia. FIG. 2v is a picture stained by the vWf antibody, using the serial section of FIG. 2u.

FIGS. 2w and 2x are stained tissue pictures of the angiosarcoma developed in human heart. In FIG. 2w, tumor cell aggregations of angiosarcoma can be observed in the LYVE-1 positive lumen, and in FIG. 2x, using the serial section of FIG. 2w and vWf staining, partly vWf positive tumor cells are also observed in the vWf positive lumen.

In FIGS. 2r-2x, the tumor cell invasion into the lymphatic vessels having LYVE-1 positive endothelial cells can be confirmed.

Magnification in each figure is as follows: a; ×550, g and s; ×350, o; ×300, j, u and v; ×250, w and x; ×225, k and p; ×185, b-d, f, l, m and q; ×130, h, i, n, r and t; ×110, e; ×50.

FIG. 3A shows LYVE-1 positive lumina observed in the connective tissue in the heart muscular tunics and in the adipose tissue of the epicardium.

FIG. 3B shows LYVE-1 positive lumina observed beneath the lung pleura, on the circumference of blood vessels or the like.

FIG. 3C shows LYVE-1 positive lumina observed on the circumference of kidney Bowman capsules and in the stroma on the circumference of renal tubules.

FIG. 3D shows LYVE-1 positive lumina observed in the stroma mainly located on the circumference of pancreas blood vessels.

FIG. 3E shows LYVE-1 positive lumina observed in the lymph nodule beneath the tonsil epithelia.

FIG. 3F shows LYVE-1 positive lumina observed in the thymus interlobular connective tissues.

FIG. 3G shows LYVE-1 positive lumina observed in all the layers from the lamina propria mucosae to the chorion of a stomach. Many are observed, especially along the muscularis mucosae and in the muscular tunics.

FIG. 3H is a stained picture of the tissues from the vicinity of the mucosal epithelia of small intestine lamina propria mucosae to the chorion stroma.

FIG. 3I shows LYVE-1 positive lumina observed within the connective tissue beneath the tongue epithelia.

FIG. 3J shows LYVE-1 positive lumina observed within the connective tissue beneath the esophagus epithelia.

FIG. 3K shows LYVE-1 positive lumina observed in the colon stroma from the mucosal substratum to the chorion.

FIG. 3L shows LYVE-1 positive lumina observed in the bladder stroma from the mucosal substratum to the chorion.

FIG. 3M shows LYVE-1 positive lumina observed in the vicinity of the blood vessels among the glandular cavities and in the capsula of the prostate gland.

FIG. 3N shows LYVE-1 positive lumina observed in the testiculus stroma on the circumference of convoluted seminiferous tubules.

FIG. 3O shows LYVE-1 positive lumina observed in the ovary cortex stroma.

FIG. 3P shows LYVE-1 positive expressing cells observed in the stroma of placenta villi stroma.

FIG. 3Q shows LYVE-1 expression observed on the endothelial cell of the lever sinusoid blood vessel.

FIG. 3R shows LYVE-1 expression observed on the endothelial cells of splenic sinus.

FIG. 3S shows LYVE-1 expression observed on the endothelial cells and the reticular cells of export and import lymphatic vessels.

FIG. 3T shows LYVE-1 expression observed on the endothelial cells of adrenal sinusoids.

FIG. 3U is a stained image showing invasion into the lymphatic vessels in the esophageal cancer. Tumor aggregations are observed in the LYVE-1 positive lumina of the tunica mucosa esophagi substrata.

FIG. 3V is a stained image showing the lymphatic vessel invasion in the stomach cancer. Tumor aggregations are observed in the LYVE-1 positive lumina in the tissue.

FIG. 3W is a figure showing the lymphatic vessel invasion in the stomach cancer EMR excised. Tumor aggregations are observed in the LYVE-1 positive lumina in the lamina propria mucosae.

FIG. 3X is the magnified picture of FIG. 3W.

FIG. 3Y is a picture showing the lymphatic vessel invasion in the cardiac angiosarcoma. Tumor aggregations are observed in the LYVE-1 positive lumina.

FIG. 3Z shows LYVE-1 expression observed partially on endothelial cells of the irregularly growing lumina in the lymphangioma.

Lane 1 and 3 are the images resulted from the reaction of the antibody reacted with the samples obtained from the LYVE-1-gene-incorporated Cos7 cells, and Lane 2 and 4 are the images with the samples obtained from the LYVE-1-gene-free Cos7 cells. Further, Lane 3 and 4 show the results of the reaction using the LYVE-1 antibody which had been reacted in advance with the excess amount of the peptide fragment according to the present invention.

Color development, observed in Lane 1 and not in Lane 3, shows that the antibody of the present invention is specific to LYVE-1 protein.

EXAMPLES

Example 1

Preparation of the Antigen

The antigen peptide fragment having the amino acid sequence according to SEQ ID NO: 1 was synthesized by Genosys ABcus 7 automatic peptide synthesizer using solid phase method. At that time, a cysteine was added to the N-terminal thereof as a linker, to give 30 mg of the antigen peptide fragment with a linker. After the synthesis, the antigen peptide fragment was purified by high performance liquid chromatography.

The antigen peptide fragment thus obtained was identified as follows:

the antigen peptide fragment was benzylated and 0.1% trifluoroacetic acid was added, and then measured by ABI Voyager System 1162 mass spectrograph.

Figure 1:
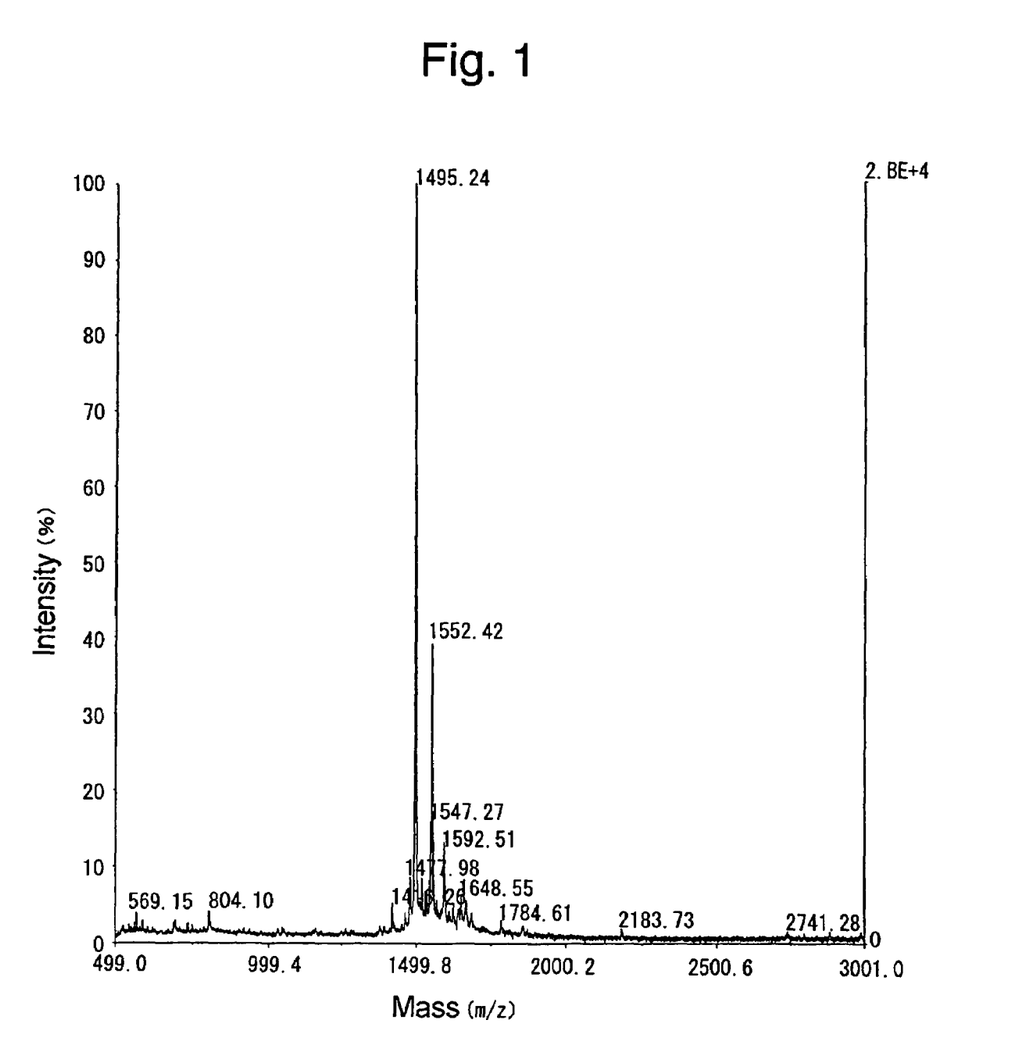
FIG. 1 shows a spectrum of the mass spectrometry of the synthesized antigen peptide, which was benzylated, added with 0.1% trifluoroacetic acid, and subjected to the mass spectrometry. The followings are the measurement conditions.

At the measurement, a standard control sample was measured to correct the difference from the theoretical molecular weight, and then the synthesized peptide fragment was measured and the agreement with the theoretical value was confirmed (see FIG. 1).

To increase the antigenicity of the synthesized antigen peptide fragment, the antigen peptide fragment was combined with a hemocyanin (KLH) through a linker and a spacer. First, the spacer and KLH were combined as follows. KLH (16 mg) was dissolved in 1 ml of 10 mM sodium phosphate buffer (pH 7.2) and 2.8 mg of MBS in dimethylformamide (1 ml) solution was added. After stirring for 30 min at room temperature, the solution was centrifuged at 16,000 rpm and the supernatant was purified by Sephadex G25 column chromatography, to give KLH-MBS coupled material (content: 1.8 mg/ml). Next, 1 mg of the above mentioned antigen peptide fragment, KLH-MBS coupled material (1 mg KLH equivalent), and ½ volume of 0.2M sodium phosphate buffer were mixed, and reacted under nitrogen gas at room temperature for 3 hrs, to give the antigen.

Example 2

Preparation of the LYVE-1 Antibody

The antigen (equivalent to 100 μg antigen peptide) was injected for immunization with the complete Freund adjuvant to the subcutis of a rabbit back.

Afterward, the antigen equivalent to 100 μg antigen peptide was injected for immunization with the incomplete Freund adjuvant in the same manner every 2 weeks, 5 times in total. Since the second immunizing injection, increase in the antibody titer was confirmed by the dot blot method using the antibody and a cellulose acetate membrane. After confirming the increase in the antibody titer, the whole blood was collected and the antiserum was separated.

Next, purification of the antibody was conducted as follows: first, the antigen peptide was attached to Affige 10 (BIO-RAD), to prepare an affinity column for purification. Then, 10 ml of decomplemented serum was diluted with equal volume of PBS (phosphate buffered saline), passed through 0.45 μm filter, and added to the affinity column. The column was washed with 50 ml PBS and then, the antibody was eluted out with 5 ml of 50 mM citrate buffer. A small amount of 2 M Tris buffer (pH 9.5) was added to the eluted antibody, so as to adjust pH of the eluted antibody solution to 7.4. By measuring O.D. of 280 nm, the antibody concentration was determined.

Example 3

Examination of the LYVE-1 Antibody Specificity

A gene containing the whole coding region of LYVE-1 protein was incorporated in the eukaryotic cell expression plasmid vector, and this plasmid vector was introduced into Cos-7 cells making use of a liposome reagent, and the LYVE-1 protein was expressed transiently. Twenty four hrs after introduction, Cos-7 cells were washed with PBS, and were lysed in a lysis buffer (a mixture of 20 mM Tris-HCl buffer, 140 mM saline, 0.1% Nonidet P-40, and 1 μg/ml protease inhibitors (pepstatin, leupeptin and aprotinin)). After centrifugation of the mixture at 15,000 rpm, the supernatant was fractionated by PAGE (polyacrylamide gel electrophoresis), and was transferred on the nylon filter, to give the filter samples. A part of these filter samples were reacted with the LYVE-1 antibody.

Meanwhile, the antibody was reacted at 4° C. overnight with the antigen peptide, to give an antibody absorption test solution, and the other part of the filter samples were reacted with the antibody absorption test solution in the same manner. Then, the filter samples were reacted with the peroxidase-labeled anti-rabbit-IgG goat serum, and then reacted with the chemiluminescence detection reagent (ECL Western blotting Kit). A lumino-image analyzer LAS-1000 (Fuji Film) was used for chemiluminescence detection. As a result, a specific band corresponding to the reaction product of LYVE-1 antibody and LYVE-1 antibody was observed on the sample filters reacted with the LYVE-1 antibody, but no such band was observed on the sample filters reacted with the antibody absorption test solution. This result proved that the antibody is a specific antibody against LYVE-1.

Example 4

Tissue Staining Using the LYVE-1 Antibody

Using paraffin fixed sections of various human normal and pathological tissues shown in the following Table 1, localization of LYVE-1 was examined.

TABLE 1

| human tissues stained by LYVE-1 | |
| --- | --- |
| Normal tissue | Malignant |
| tongue, esophagus, stomach, small intestine, colon, | esophageal cancer, stomach cancer, lung cancer, |

TABLE 1-continued

| human tissues stained by LYVE-1 | |
| --- | --- |
| Normal tissue | Malignant |
| heart, lung, kidney, bladder, prostate grand, testis, ovarium, placenta, pancreas, liver, spleen, adrenal grand, tonsil, thymus, lymph node | angiosarcoma (heart), lymphatic vessel (lymphangioma) |

Each section was deparaffinized and then placed on a glass slide, and the tissue on the glass slide was reacted with the LYVE-1 antibody at room temperature for 30 min. After washed by PBS, this was reacted with the biotin-labeled anti-rabbit-IgG goat serum at room temperature for 30 min.

Figure 2:
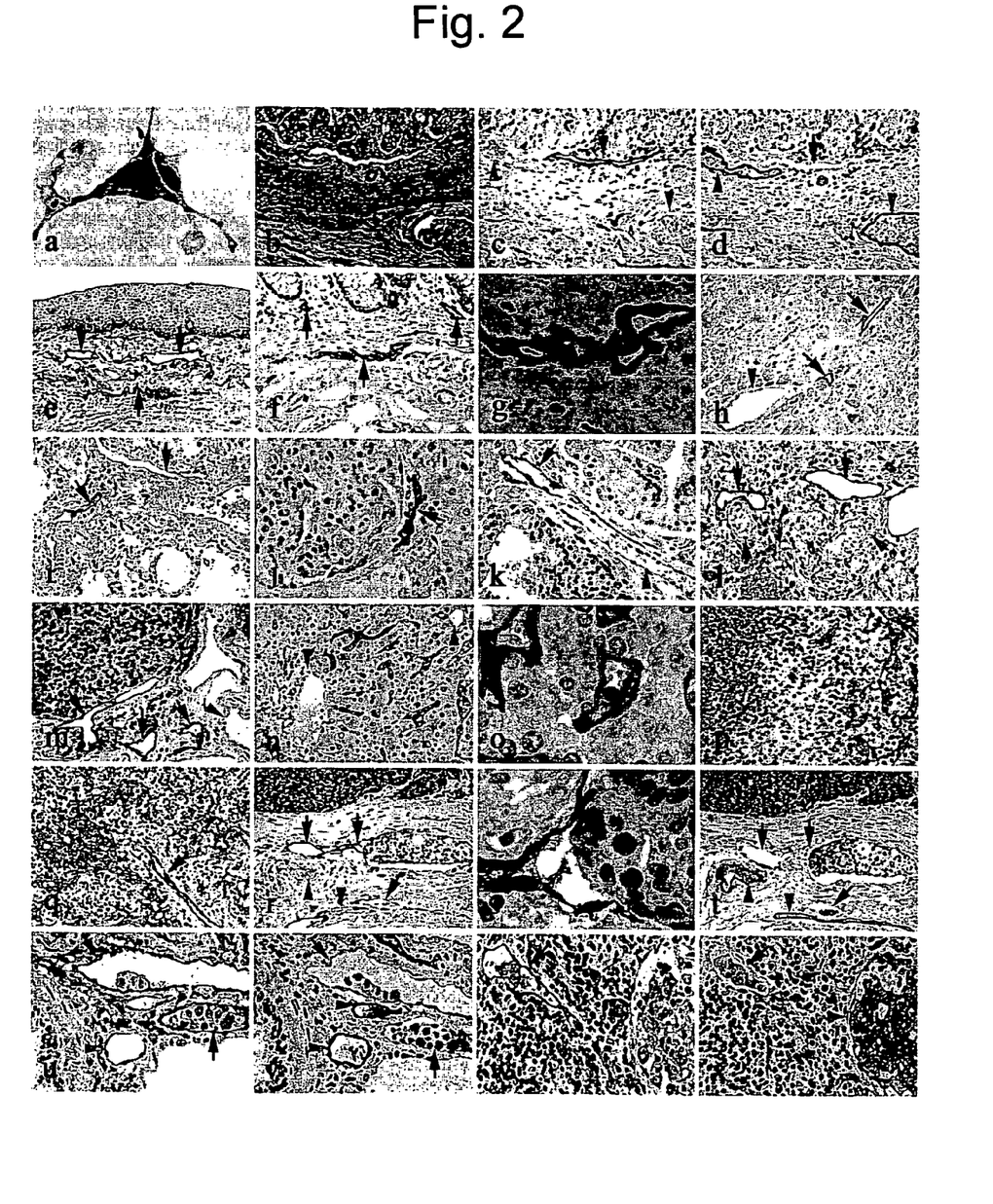
FIG. 2 are stained pictures of various human normal and malignant tumor tissues stained using the antibody of the present invention. In each of the stained pictures in FIG. 2, an arrow points to a lymphatic vessel stained by the LYVE-1 antibody, and arrowhead a blood vessel stained by von Willebrad factor (vWf).

The reaction product was washed by PBS, and further reacted with a streptavidin-peroxidase coupling reagent at room temperature for 30 min. After washing by PBS, the color was developed using 3,3-diaminobenzidine hydrochloride as the substrate. Stained images of various tissues are shown in FIG. 2.

In order to compare the staining of the lymphatic vessel endothelial cells with the staining of the blood vessel endothelial cells in the same tissue, staining of the blood vessel endothelial cells by von Wilebrand factor (vWf) was also conducted in a similar way.

Figure 3:
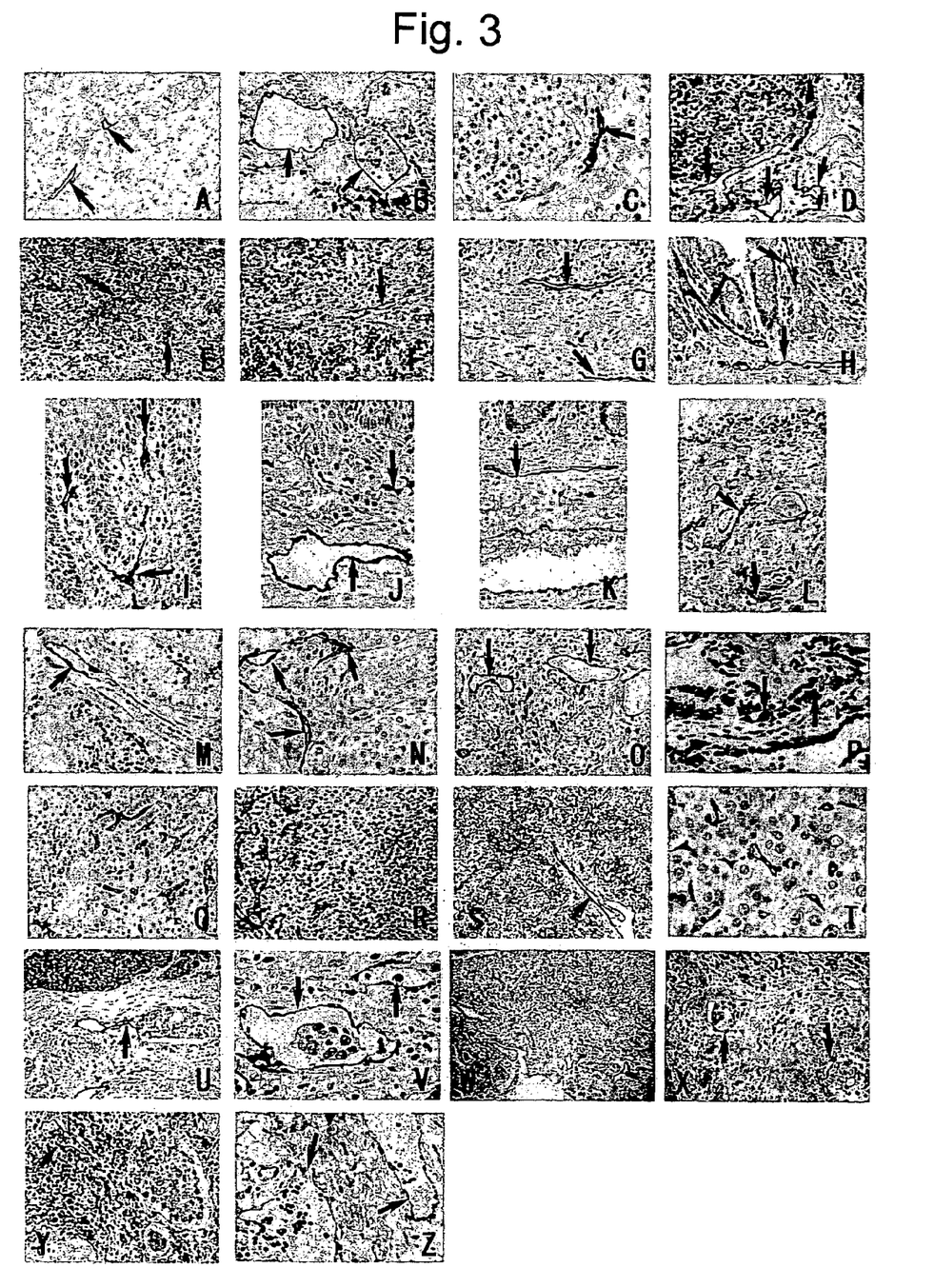
Figure 4:
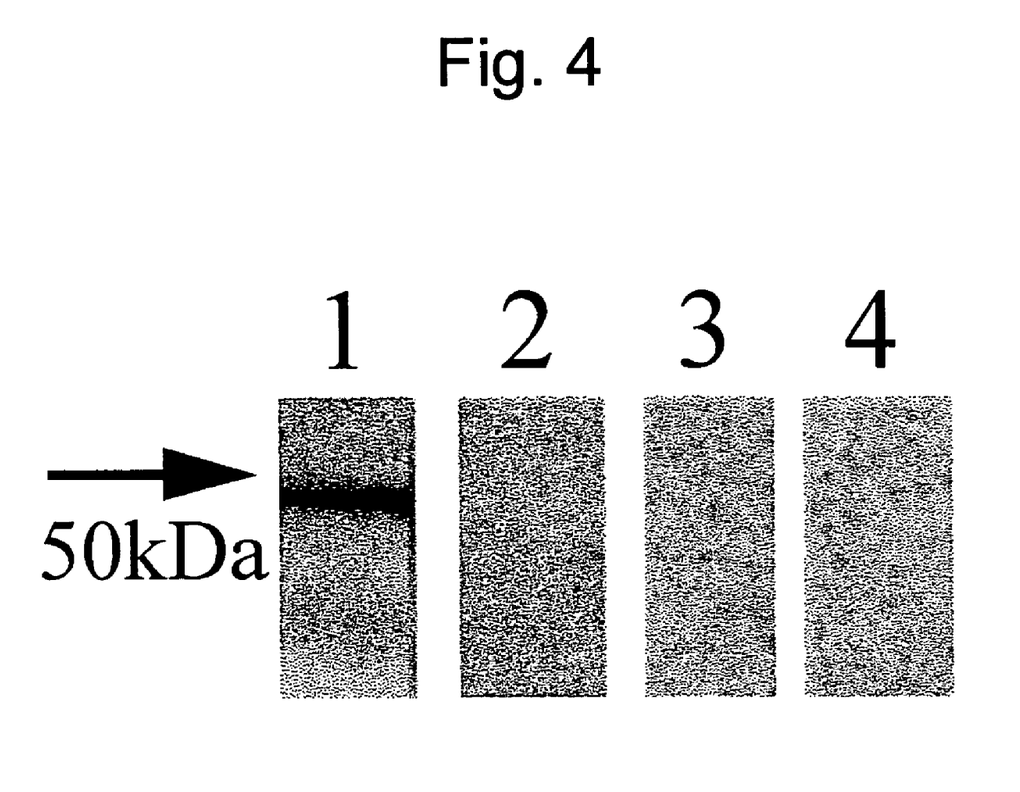
FIG. 4 shows Western blot images by which specificity of the antibody was confirmed.

As a result, at various human tissues in both normal and pathological conditions, the lymphatic vessel endothelial cells were stained by the LYVE-1 antibody, but none of the blood vessel endothelial cells were stained. Also, the blood vessel endothelial cells were stained by vWf, but the lymphatic vessel endothelial cells were not. Stained images of each tissue are shown in FIG. 3.

The results of experiments described above have proved that the LYVE-1 antibody is an antibody to recognize specifically the lymphatic vessel endothelial cells and that the LYVE-1 antibody is useful to specify the cancer cell invasion regions in the lymphatic vessels.

The present invention provides peptide fragments of LYVE-1 and antibody thereto. Making use of the antibody of the present invention, only the lymphatic vessels in the living tissues can be selectively stained. Especially, the antibody of the present invention is valuable for the usage to obtain pathological findings about the destructive and invasive growth of the lymphatic vessel by the malignant in a living tissue, and in its turn, indicators for diagnosing the degree of malignancy may be obtained using the antibody of the present invention, and thus, said antibody will become useful for the treatment and prognosis of cancer patients.

Moreover, the antibody of the present invention can be used for the lymphangiogenesis treatment utilizing isolation and purification of the human lymphocytes. That is, making use of the antibody of the present invention, the lymphatic vessel cells and the precursor cells thereof are isolated by means of a cell sorter, a magnetic cell separation method or the like, and can be used, for example, for the lymphangiogenesis treatment aimed to reduce the lymphatic vessel edema and the like. (Lymphangiogenesis in tumors: What do we know?, Microscopy Research and Technique, Volume 60, Issue 2, 171-180, February 2003; Lymphangiogenesis and Tumor Metastasis, Myth or Reality?, Clinical Cancer Research Vol. 7, 462-468, March 2001; Expression of the Fms-Like Tyrosine Kinase 4, Gene Becomes Restricted to Lymphatic Endothelium During Development, Proceedings of the National Academy of Sciences, Vol. 92, 3566-3570, April, 1995)

The invention claimed is:

1. An isolated peptide fragment consisting of the amino acid sequence of SEQ ID NO:1.

2. An isolated peptide comprising the peptide fragment consisting of the amino acid sequence of SEQ ID NO: 1 and a linker.

* * * * *